United States Patent [19]

Crombie et al.

[11] Patent Number: 6,096,892
[45] Date of Patent: Aug. 1, 2000

[54] CHEMICAL PROCESS

[75] Inventors: Barry Stuart Crombie; David John Ritchie, both of Falkirk; Raymond Vincent Heavon Jones, West Lothian, all of United Kingdom

[73] Assignee: Zeneca Limited, United Kingdom

[21] Appl. No.: 09/191,491

[22] Filed: Nov. 13, 1998

Related U.S. Application Data

[63] Continuation of application No. PCT/GB97/01136, Apr. 24, 1997.

[30] Foreign Application Priority Data

May 17, 1996 [GB] United Kingdom .................. 9610320

[51] Int. Cl.⁷ ................................................. C07D 239/52
[52] U.S. Cl. .............................................................. 544/319
[58] Field of Search ............................................. 544/319

[56] References Cited

U.S. PATENT DOCUMENTS 4,059,696 11/1977 Maurer et al. ........................... 424/200

FOREIGN PATENT DOCUMENTS

| 798724 | 2/1994 | Belgium . |
|---|---|---|
| 1082031A | 2/1994 | China . |
| 0 738 717 A1 | 10/1996 | European Pat. Off. . |
| 0 816 345 A1 | 1/1998 | European Pat. Off. . |
| 1 200 308 | 4/1966 | Germany . |
| 1092144 | 11/1967 | United Kingdom . |

OTHER PUBLICATIONS

Chemical Abstracts, vol. 38: 4565h, 1963 (Partial Translation of Article).
Chemical Abstracts, vol. 65: 727f, 1966.
Chemical Abstracts, vol. 90: 49472c, 1979.
Hennart & Merlin, "Contribution ``la synthèse de la dichloro–4–6 pyrimidine", Mémoires Présentés A La Société Chimique, 741 to 742 (1958) and partial translation.
M. Prystas, "N–Alkyl Derivatives of 2–and 5–Substituted 4–Hydroxy–6(1H)–Pyrimidinomes", Collection Czechoslov. Chem. Commun., 32 at 4241–4259 (1967).
Zhim. Farm. Zh. (1974) 8(12)28–31 and partial translation.
Vladimirtsev et al., Fiziol. Akt. Veshchestva, 1978, 45–47 and translation.
Hull, J. Chem. Soc., A New Sunthesis of 4: 6–Dihydroxypyrimidines, 1951, 2214.
H. Gershon, R. Brown. A. Scala, & R. Rodin, Pyrimidines. IV. 2–, 5–, and 2,5–Substituted Chloropyrimidines, 7 J. Med. Chem. At 808–11 (1964).

*Primary Examiner*—John M. Ford
*Attorney, Agent, or Firm*—David P. LeCroy

[57] ABSTRACT

A process for preparing 4,6-dihydroxypyrimidine comprising the steps:
  a) contacting formamide, an alkoxide of formula ROM and a malonate of formula $CH_2(CO_2R)_2$ in a solvent of formula ROH;
  b) adding water to the product of step (a);
  c) removing substantially all of the solvent of formula ROH from the product of step (b); and
  d) acidifying the product of step (c)
wherein R is $C_{1-4}$ alkyl and M is an alkali metal.

9 Claims, No Drawings

CHEMICAL PROCESS

This application is a continuation of international application number PCT GB97/01136, filed Apr. 24, 1997, (status, abandoned, pending, ect.).

The present invention concerns a process for making 4,6-dihydroxypyrimidine. 4,6-Dihydroxypyrimidine is a useful chemical intermediate (especially in the agrochemical industry).

Various processes for making 4,6-dihydroxypyrimidine, and substituted variants thereof, have been disclosed. See for example U.S. Pat. No. 4,059,696, GB1092144, Chem.Abs. (1963) 58 4565h, J.Med.Chem. (1964) 7(6) 808–11, Bull.Soc.Chim.France (1959) 741–2, Collect.Czech.Chem-.Commun. (1967) 32(12) 4241–59, Zhim. Farm. Zh.(1974) 8(12) 28–31, BE-798724, CN1082031, EP-A1-0738717 and J.Chem.Soc. (1951) 2214.

The present invention provides a process for preparing 4,6-dihydroxypyrimidine comprising the steps:

a) contacting formamide, an alkoxide of formula ROM and a malonate of formula $CH_2(CO_2R)_2$ in a solvent of formula ROH;

b) adding water to the product of step (a);

c) removing substantially all of the solvent of formula ROH from the product of step (b); and d) acidifying the product of step (c)

wherein R is $C_{1-4}$ alkyl and M is an alkali metal.

The addition of water before the removal of the solvent of formula ROH enables more organic material to be recovered during step (c) because the following reaction takes place:

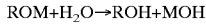

$$ROM + H_2O \rightarrow ROH + MOH$$

wherein R and M are as defined above.

Alkyl groups contain from 1 to 4 carbon atoms and are straight or branched chain. Alkyl is, for example, methyl or ethyl, but is preferably methyl.

Alkali metals are, for example, sodium or potassium.

Step (a) of the process of the invention can be conducted in a number of ways but it is preferred that:

i) formamide is contacted with an alkoxide of formula ROM in a solvent of formula ROH; and ii) the product of (i) is contacted with a malonate of formula $CH_2(CO_2R)_2$.

It is preferred that malonate of formula $CH_2(CO_2R)_2$ is added to the product of (i) at an elevated temperature (such as a temperature in the range 40–80° C., especially 40–60° C.).

It is preferred that the molar ratio of formamide:ROM:$CH_2(CO_2R)_2$ in step (a) is in the range (2.0–4.0):(3.0–4.0):(0.8–1.2), especially in the range (3.0–3.2):(3.3–3.7):(0.9–1.1), more preferably about 3:3.5:1.

A preferred method for solvent removal (step (c) of the present invention) is distillation, especially distillation under reduced pressure. Substantially all of the solvent of formula ROH is removed when more than 95% (preferably more than 98%) is removed. When the solvent of formula ROH is removed water may also be removed to leave a solid residue, an aqueous slurry or a solution in water. (It is preferred that not all the water is removed, that is, that after removal of the solvent of formula ROH an aqueous slurry or a solution in water remains.) Water is added to the solid residue or aqueous slurry so that complete dissolution is achieved before step (d) is carried out.

Acidification (step (d)) of the product of step (c) of the present invention is preferably acidification to a pH in the range 1–5 (for example 1.54.0), especially in the range 2–3, particularly about 2.1. While acidification can be carried out using a suitable ion exchange resin it is preferred that a strong mineral acid (such as nitric acid, hydrochloric acid or sulphuric acid), or a suitable organic acid (such as acetic acid) is used.

When the product of step (c) is acidified 4,6-dihydroxypyrimidine precipitates. In order to reduce co-precipitation of inorganic materials it is preferred (especially when sulphuric acid is used for the acidification) to keep the temperature above 25° C. (especially in the range 30–40° C.). In this way, it is possible to obtain product that can be used as a chemical intermediate without the need for further purification.

The acidification in step (d) can be achieved by the addition of a suitable acid to the product of step (c) or, preferably, by the addition of the product of step (c) to a suitable acid.

In one aspect the present invention provides a process for preparing 4,6-dihydroxypyrimidine, the process comprising adding a malonate of formula $CH_2(CO_2R)_2$ to a mixture of formamide and an alkoxide of formula ROM in a solvent of formula ROH at an elevated temperature and heating the resulting mixture at an elevated temperature (especially in the range 40–80° C.). After a suitable length of time water is added to the resulting mixture and substantially all the solvent of formula ROH removed to leave an aqueous slurry. If necessary water is added to the aqueous residue to ensure that all solids are in solution and the solution is acidified and 4,6-dihydroxypyrimidine precipitates out. The product can be collected by filtration.

The following Examples illustrate the invention. Where provided, nuclear magnetic resonance (NMR) data are expressed in parts per million (ppm) from tetramethylsilane.

EXAMPLE 1

To a stirred solution of sodium methoxide (140 g, 0.7 mol of a 27% solution in methanol) under nitrogen was added formamide (27.0 g, 0.6 mol) over about 5 minutes. The resulting reaction mixture was heated to 50° C. and then dimethyl malonate (26.4 g, 0.2 mol) added dropwise over 1 hour. The resulting white suspension was held at 50° C. for a further hour and then cooled to ambient temperature. Water (100 ml) was added to dissolve all the solid and the resulting straw-coloured solution was stirred for about 15 minutes and then the methanol was removed under vacuum (final pot at 50° C. under 100 mmHg vacuum). Water (40 ml) was added and then 36% sulphuric acid (90 g) added to give a final pH of 2.2. Once the acid had been added the temperature was kept at about 35° C. The yellow suspension was stirred for 1 hour, filtered and washed with water (2×25 g). The water-wet paste was dried overnight under vacuum at 50° C. to provide 4,6-dihydroxypyrimidine (16.2 g, 70% yield, 96% strength).

EXAMPLE 2

To a stirred solution of sodium methoxide (63 g of a 30% solution in methanol containing 0.35 mol) under nitrogen was added formamide (13.5 g, 0.3 mol) over 5 minutes. The resulting reaction mixture was heated to 50° C. and then dimethyl malonate (13.2 g, 0.1 mol) added dropwise over 1 hour. The resulting white suspension was held at 50° C. for a further hour and then cooled to ambient temperature. Water (50 ml) was added to dissolve all the solid and the resulting straw-coloured solution was stirred for about 15 minutes and then methanol was removed under vacuum (final pot at 50°

C. under 100 mmHg vacuum) until signs of solid could be seen. Water (20 ml) added and then 36% hydrochloric acid added to give a final pH of 2.1. The resulting yellow suspension was stirred for 1 hour, filtered and washed with water (2×15 ml). The water-wet paste was dried overnight under vacuum at 50° C. to provide 4,6-dihydroxypyrimidine (8.75 g at 96.2% strength, 75.1% yield).

EXAMPLE 3

To a stirred solution of sodium methoxide (252 g of a 30% solution in methanol containing 1.4 mol) under nitrogen was added formamide (54.0 g, 1.2 mol) over 5 minutes. The resulting reaction mixture was heated to 50° C. and then dimethyl malonate (52.8 g, 0.4 mol) added dropwise over 1 hour. The resulting white suspension was held at 50° C. for a further hour and then cooled to ambient temperature. Water (200 ml) was added to dissolve all the solid and the resulting straw-coloured solution was stirred for about 15 minutes and then methanol was removed under vacuum (final pot at 40° C. under 100 mmHg vacuum) until no further distillation was seen. Water (80 ml) was then added to leave a straw-coloured opaque solution (355.6 g) which was used in Acidifications (a), (b) and (c) below.

Acidification (a)

A sample of the straw-coloured opaque solution (118.8 g, 0.134 mol based on dimethyl malonate starting material) was charged to a flask and the pH adjusted to 2.1 using 36% hydrochloric acid. The yellow slurry produced was agitated for an hour, filtered and washed with water (2×15 ml). The water-wet paste was dried overnight under vacuum at 50° C. to afford 4,6-hydroxypyrimidine (12.0 g at 95.5% strength, 76.4% yield).

Acidification (b)

A sample of the straw-coloured opaque solution (108.1 g, 0.122 mol based on dimethyl malonate starting material) was charged to a flask and water (50 ml) was added. The pH was then adjusted to 2.1 using 36% hydrochloric acid. The yellow slurry produced was agitated for an hour, filtered and washed with water (2×15 ml). The water-wet paste was dried overnight under vacuum at 50° C. to afford 4,6-dihydroxypyrimidine (10.4 g at 98.3% strength, 74.8% yield).

Acidification (c)

A sample of the straw-coloured opaque solution (127.1 g, 0.143 mol based on dimethyl malonate starting material) was added dropwise to 36% hydrochloric acid (50 g) over 30 minutes. The pH at the end of addition was found to be 1.9. The very pale yellow slurry produced was agitated for an hour, filtered and washed with water (2×15 ml). The water-wet paste was dried overnight under vacuum at 50° C. to afford 4,6 -dihydroxypyrimidine (12.3 g at >99% strength, 76.0% yield).

EXAMPLE 4

To a stirred solution of sodium methoxide in methanol (126.3 g of a 30% solution containing 0.7 mol) under nitrogen was added formamide (27.0 g, 0.6 mol) over 5 minutes. The resulting reaction mixture was heated to 50° C. and then dimethyl malonate (26.4 g, 0.2 mol) was added dropwise over 1 hour. The resulting white suspension was held at 50° C. for an hour and then cooled to ambient temperature. A white solid was isolated by filtration and was washed with methanol (50 g). The solid was then dried under vacuum overnight.

$^1$H NMR ($D_2O$):δ 8.2, 7.7 and 4.9 ppm.

$^{13}$C NMR (D2O):δ 174.7, 170.0, 155.3 and 90.5 ppm.

The following preparations were conducted for comparative purposes.

A $D_2O$ solution of the disodium salt of 4,6-dihydroxypyrimidine was prepared by treating a sample of 4,6-dihydroxypyrimidine with a solution of a suitable amount of sodium hydroxide in $D_2O$. Proton NMR of the resulting solution showed peaks at 7.4(H-2) and 4.7(H-5) ppm.

A $D_2O$ solution of the dipotassium salt of 4,6-dihydroxypyrimidine was prepared by treating a sample of 4,6-dihydroxypyrimidine with a solution of a suitable amount of potassium hydroxide in $D_2O$. $^{13}$C NMR of the resulting solution showed peaks at 179.2(C-4 & C-6), 160.9 (C-2) and 93.8(C-5) ppm.

Proton NMR of a solution of 4,6-dihydroxypyrimidine in dimethylsulphoxide (DMSO) showed peaks at 8.0(H-2) and 5.2(H-5) ppm.

What is claimed is:

1. A process for preparing 4,6-dihydroxypyrimidine comprising the steps:
   a) contacting formamide, an alkoxide of formula ROM and a malonate of formula $CH_2(CO_2R)_2$ in a solvent of formula ROH;
   b) adding water to the product of step (a);
   c) removing substantially all of the solvent of formula ROH from the product of step (b); and
   d) acidifying the product of step (c)
   wherein R is $C_{1-4}$ alkyl and M is an alkali metal.

2. A process as claimed in claim 1 wherein R is methyl or ethyl.

3. A process as claimed in claim 1 wherein M is sodium or potassium.

4. A process as claimed in claim 1, wherein step (a) comprises:
   i) contacting formamide with an alkoxide of formula ROM in a solvent of formula ROH; and
   (ii) contacting the product of (i) with a malonate of formula $CH_2(CO_2R)_2$.

5. A process as claimed in claim 1, wherein the acid used in step (d) is sulphuric acid.

6. A process as claimed in claim 1, wherein the molar ratio of formamide:
   ROM:$CH_2(CO_2R)_2$ in step (a) is in the range: (2.0–4.0):(3.0–4.0):(0.8–1.2).

7. A process as claimed in claim 1, wherein distillation under reduced pressure is employed in step (c).

8. A process as claimed in claim 1, wherein the acidification of step (d) is to a pH in the range 1–5.

9. A process as claimed in claim 1 wherein the product of step (d) is kept at a temperature above 25° C. while 4,6-dihydroxypyrimidine is isolated.

* * * * *